US012226267B2

(12) United States Patent
Torrie et al.

(10) Patent No.: US 12,226,267 B2
(45) Date of Patent: Feb. 18, 2025

(54) METHODS AND SYSTEMS FOR FIDUCIAL MARKER DEPLOYMENT IN MEDICAL PROCEDURES

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Paul Alexander Torrie, Marblehead, MA (US); Philip A. Cormier, Newburyport, MA (US); Rafal Z. Jezierski, Candia, NH (US); Nathan Zamarripa, Kittery Point, ME (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 0 days.

(21) Appl. No.: 18/695,553

(22) PCT Filed: Nov. 3, 2022

(86) PCT No.: PCT/US2022/079240
§ 371 (c)(1),
(2) Date: Mar. 26, 2024

(87) PCT Pub. No.: WO2023/114584
PCT Pub. Date: Jun. 22, 2023

(65) Prior Publication Data
US 2024/0325109 A1    Oct. 3, 2024

Related U.S. Application Data

(60) Provisional application No. 63/289,862, filed on Dec. 15, 2021.

(51) Int. Cl.
*A61B 17/88* (2006.01)
*A61B 90/00* (2016.01)

(52) U.S. Cl.
CPC .......... *A61B 90/39* (2016.02); *A61B 17/8883* (2013.01); *A61B 17/8888* (2013.01);
(Continued)

(58) Field of Classification Search
CPC .. A61B 17/8883; A61B 17/8888; A61B 90/39
See application file for complete search history.

(56) References Cited

U.S. PATENT DOCUMENTS 7,577,473 B2    8/2009  Davis et al.
8,480,716 B2    7/2013  Perrow et al.
(Continued)

FOREIGN PATENT DOCUMENTS

WO        9836371 A1    8/1998

OTHER PUBLICATIONS

International Search Report and Written Opinion mailed Feb. 21, 2023 for International Application No. PCT/US2022/079240, 14 pages.

*Primary Examiner* — Sameh R Boles
(74) *Attorney, Agent, or Firm* — Dickinson Wright PLLC; Charles W. Kocher, II (57) ABSTRACT

A marker deployment system and method of operation are provided. The system includes a handle extending radially from and longitudinally along a main axis. A driver tube is coupled to and extends from the handle along the main axis from a proximal tube end to a distal tube end and defines a tube bore extending axially therethrough. The distal tube end is configured to support a bone marker. An inner rod extends axially through the driver tube to a distal rod end that includes a retention fastener configured to engage and selectively secure the bone marker at the distal tube end. A
(Continued)

knob is operably coupled to the inner rod and is rotatable about a knob axis of rotation extending along the main axis to secure or release the bone marker. At least a portion of the handle extends axially beyond the knob to define the proximal handle end.

5 Claims, 9 Drawing Sheets

(52) U.S. Cl.
CPC ............... *A61B 2090/3916* (2016.02); *A61B 2090/3987* (2016.02); *A61B 2090/3991* (2016.02)

(56) References Cited

U.S. PATENT DOCUMENTS

| | | |
|---|---|---|
| 8,529,465 B2 | 9/2013 | Speeg et al. |
| 8,540,756 B2 | 9/2013 | Olsen et al. |
| 8,696,681 B2 | 4/2014 | Harris et al. |
| 9,993,232 B2 | 6/2018 | Ellingson et al. |
| 9,999,758 B2 | 6/2018 | Vetter et al. |
| 10,335,124 B1 | 7/2019 | Robinson et al. |
| 2012/0184963 A1* | 7/2012 | Burgi ................ A61F 2/4609 606/91 |
| 2020/0009376 A1 | 1/2020 | Chang et al. |
| 2021/0378704 A1 | 12/2021 | Laviola et al. |

* cited by examiner

METHODS AND SYSTEMS FOR FIDUCIAL MARKER DEPLOYMENT IN MEDICAL PROCEDURES

CROSS-REFERENCE TO RELATED APPLICATIONS

This application is a U.S. National phase entry of PCT Application No. PCT/US2022/079240 filed Nov. 3, 2022 titled, "Methods and Systems for Fiducial Marker Deployment in Medical Procedures." The PCT application claims the benefit of U.S. Provisional Application No. 63/289,862 filed Dec. 15, 2021 titled "Methods and Systems for Fiducial Marker Deployment in Medical Procedures." Both applications are incorporated by reference herein as if reproduced in full below

BACKGROUND

Arthroscopic surgical procedures are minimally invasive surgical procedures in which access to the surgical site within the body is by way of small keyholes or ports through the patient's skin. The various tissues within the surgical site are visualized by way of an arthroscope placed through the port, and the internal scene is shown on an external display device. The tissue may be repaired or replaced through the same or additional ports.

In computer-assisted surgical procedures (e.g., replacement of the anterior cruciate ligament (ACL), reduction of femora-acetabular impingement), the location of various objects with the surgical site may be tracked by way of images captured by the arthroscope. In particular, related-art systems teach tracking location of objects (e.g., medical instruments, bone) based on reading a quick response code (QR code), determining the orientation of the QR code within the three-dimensional coordinate space, and then determining the location and/or orientation of the attached instrument or bone within the three-dimensional coordinate space.

Bone markers including such QR codes may include a threaded anchor portion configured to be secured in a bone when driven by a corresponding installation tool or marker deployment system. Markers may further include an internal threaded portion that is engaged by a threaded rod of the marker deployment system. The threaded rod may be rotated independently of the marker deployment system, to temporarily secure the marker in the marker deployment system until the bone marker has been deployed.

However, rotation of threaded rod to disengage the marker while holding a handle of the driver tool is inconveniently a two-handed operation.

SUMMARY

A first example is a marker deployment system, comprising: a handle extending radially from and longitudinally along a main axis from a proximal handle end to a distal handle end; a driver tube coupled to and extending from the handle at the distal handle end along the main axis from a proximal tube end to a distal tube end and defining a tube bore extending axially therethrough, the distal tube end configured to support a bone marker; an inner rod extending axially through the driver tube from a proximal rod end to a distal rod end including a plurality of distal rod threads comprising a retention fastener configured to engage and selectively secure the bone marker at the distal tube end; and a knob operably coupled to the inner rod and rotatable about a knob axis of rotation extending along the main axis in a first direction to secure the bone marker and in a second direction opposite the first direction to release the bone marker, wherein at least a portion of the handle extends axially beyond the knob to define the proximal handle end.

In the first example marker deployment system, the knob axis of rotation may be offset and parallel to the main axis, the inner rod may include a plurality of rod teeth extending radially outwardly therefrom adjacent the proximal rod end, the knob may be annularly shaped to define a knob opening, the knob may include a plurality of knob teeth extending radially inwardly into the knob opening and configured to meshingly engage one or more of the plurality of rod teeth to rotate the inner rod about the main axis as the knob is rotated about the knob axis of rotation. The handle may define a handle cavity extending along the main axis and the driver tube extends axially into the handle cavity; the driver tube may include a top tube portion and a bottom tube portion and may define a gear window extending through the driver tube into the tube bore, the gear window disposed on the top tube portion and configured to enable the plurality of knob teeth to meshingly engage the one or more of the plurality of rod teeth; the handle may extend radially outwardly to a peripheral surface configured to be held in one hand of a user; the handle may include a knob support wall extending radially outwardly from the handle cavity to the peripheral surface proximate the distal handle end of the handle; the handle may include a tube support portion extending axially away from the knob support wall and along the bottom tube portion of the driver tube and through the knob opening to define the distal handle end of the handle and configured to abut at least some of the plurality of knob teeth; and at least one of the knob and the handle may be configured to retain the knob axially and enable the user to turn the knob with the one hand and enable rotation of the knob about the knob axis of rotation.

In the first example marker deployment system, the knob axis of rotation may be coaxial with the main axis, the knob may be configured to rotate with the inner rod and movable axially along the handle, the handle may define a handle cavity extending axially through the distal handle end to a linear translation portion including a plurality of handle threads defined therein, and the proximal rod end may extend past the proximal tube end of the driver tube and at least partially into the linear translation portion of the handle cavity and may include a plurality of proximal rod threads configured to threadingly engage one or more of the plurality of handle threads and cause simultaneous rotation about and axial translation of the inner rod along the main axis as the knob is rotated about the knob axis of rotation. The driver tube may partially extend axially into the handle cavity; the handle may extend radially outwardly a first diameter to a peripheral surface be configured to be held in one hand of a user; the handle may include a knob sliding portion having a second diameter less than the first diameter to define a distal knob shoulder between the peripheral surface and the knob sliding portion and a proximal knob shoulder between the peripheral surface and the knob sliding portion, the distal knob shoulder may be configured to abut the knob in a marker locked position of the knob and the proximal knob shoulder may be configured to abut the knob in a marker unlocked position of the knob; the knob may extend radially outwardly a third diameter greater than the first diameter and may be annularly shaped to define a knob opening configured to surround and slidingly abut the knob sliding portion and may include at least one knob pin extending radially inwardly; and the knob sliding portion may define at least one rod engagement slot and the at least one knob pin may extend through the at least one rod engagement slot and attach the knob to the inner rod to fix the inner rod for rotation with the knob and may be configured to enable the user to turn the knob with the one hand and provide limited axial movement of the knob as the knob is simultaneously rotated about the knob axis of rotation and axially translated along the main axis.

In the first example marker deployment system, the plurality of proximal rod threads may be different than the plurality of handle threads of the linear translation portion of the handle cavity.

In the first example marker deployment system, the driver tube may partially extend axially into the handle cavity; the handle may extend radially outwardly a first diameter to a peripheral surface configured to be held in one hand of a user; the handle may include a distal knob barrier within the handle cavity and extend radially inwardly from the peripheral surface and a proximal knob barrier within the handle cavity and extending radially inwardly from the peripheral surface, the distal knob barrier may be configured to abut the knob in a marker locked position of the knob and the proximal knob barrier may be configured to abut the knob in a marker unlocked position of the knob; the knob may extend radially outwardly from the inner rod a third diameter less than the first diameter and may be configured to rotate in the handle cavity; and the handle may define at least one knob access window extending radially inwardly from the peripheral surface into the handle cavity and may be configured to enable the user to turn the knob with the one hand and provide limited axial movement of the knob as the knob is simultaneously rotated about the knob axis of rotation and axially translated along the main axis.

In the first example marker deployment system, the knob axis of rotation may be coaxial with the main axis, the knob may be configured to rotate with the inner rod, the handle may include a free swivel coupled to the handle and extend axially beyond the knob to define the proximal handle end, the free swivel may be rotatable about the main axis completely independently from rotation of the knob and the handle, and rotation of the knob may cause rotation of the inner rod about the main axis as the knob is rotated about the knob axis of rotation.

A second example is a marker deployment system, comprising: a handle extending radially from and longitudinally along a main axis from a proximal handle end to a distal handle end to define a proximal half of the handle adjacent the proximal handle end and a distal half of the handle adjacent the distal handle end; a driver tube coupled to and extending from the handle at the distal handle end along the main axis from a proximal tube end to a distal tube end and defining a tube bore extending axially therethrough, the distal tube end configured to support a bone marker; an inner rod extending axially through the driver tube from a proximal rod end to a distal rod end including a plurality of distal rod threads comprising a retention fastener configured to engage and selectively secure the bone marker at the distal tube end; and a knob operably coupled to the inner rod and rotatable about a knob axis of rotation extending along the main axis in a first direction to secure the bone marker and in a second direction opposite the first direction to release the bone marker, the knob disposed in the distal half of the handle.

In the second example marker deployment system, the knob axis of rotation may be offset and parallel to the main axis, the inner rod may include a plurality of rod teeth extending radially outwardly therefrom adjacent the proximal rod end, the knob may be annularly shaped to define a knob opening, the knob may include a plurality of knob teeth extending radially inwardly into the knob opening and may be configured to meshingly engage one or more of the plurality of rod teeth to rotate the inner rod about the main axis as the knob is rotated about the knob axis of rotation.

In the second example marker deployment system, the knob axis of rotation may be coaxial with the main axis, the knob may be configured to rotate with the inner rod and movable axially along the handle, the handle may define a handle cavity extending axially through the distal handle end to a linear translation portion including a plurality of handle threads defined therein, the proximal rod end may extend past the proximal tube end of the driver tube and at least partially into the linear translation portion of the handle cavity and may include a plurality of proximal rod threads configured to threadingly engage one or more of the plurality of handle threads and cause simultaneous rotation about and axial translation of the inner rod along the main axis as the knob is rotated about the knob axis of rotation. The driver tube may partially extend axially into the handle cavity; the handle may extend radially outwardly a first diameter to a peripheral surface configured to be held in one hand of a user; the knob may extend radially outwardly from the proximal rod end a third diameter less than the first diameter and is may be configured to rotate in the handle cavity; and the handle may include at least one knob access window extending radially inwardly from the peripheral surface into the handle cavity and may be configured to enable the user to turn the knob with the one hand and provide limited axial movement of the knob as the knob is simultaneous rotated and axially translated along the main axis as the knob is rotated about the knob axis of rotation.

Yet another example is a method of operating a marker deployment system, the method comprising: telescoping a bone marker into an internal volume at a distal end of the marker deployment system, the bone marker comprising a polyhedron and an externally-threaded screw extending distally from the polyhedron and a retention bore having an entrance aperture through an upper face of the polyhedron; turning a knob in a first direction about a knob axis of rotation, the knob operably coupled to an inner rod extending along a main axis of the marker deployment system from a proximal rod end through a distal handle end of a handle and a driver tube of the marker deployment system to a distal rod end defining a retention fastener and at least a portion of the handle extends axially beyond the knob to define a proximal handle end; placing the retention fastener within the retention bore of the bone marker in response to turning the knob in the first direction, the retention fastener retains the bone marker in a mating relationship with the marker deployment system; positioning a distal end of the externally-threaded screw against a bone at a marker location; and screwing the externally-threaded screw into the bone by way of the marker deployment system.

In the example method, the step of turning a knob in a first direction about a knob axis of rotation extending along a main axis of the marker deployment system may further comprise grasping a peripheral surface of a handle of the marker deployment system with one hand of a user and turning the knob in the first direction about the knob axis of rotation extending along the main axis of the marker deployment system using the one hand of the user.

The example method may further comprise, after screwing the externally-threaded screw into the bone: turning the knob in a second direction about the knob axis of rotation opposite the first direction; and removing the retention fastener from within the retention bore in response to turning the knob in the second direction. The step of turning the knob in a second direction about the knob axis of rotation opposite the first direction may further comprise grasping a peripheral surface of a handle of the marker deployment system with one hand of a user and turning the knob in the second direction about the knob axis of rotation opposite the first direction using the one hand of the user.

In the example method, placing the retention fastener within the retention bore of the bone marker in response to turning the knob in the first direction may further comprise threading distal rod threads of the retention fastener into mating relationship with internal threads of the retention bore.

In the example method, the knob axis of rotation may be offset and parallel to the main axis, the inner rod may include a plurality of rod teeth extending radially outwardly therefrom adjacent the proximal rod end, the knob may be annularly shaped to define a knob opening, the knob may include a plurality of knob teeth extending radially inwardly into the knob opening and configured to meshingly engage one or more of the plurality of rod teeth, the method may further comprise rotating the inner rod about the main axis in response to the knob being rotated about the knob axis of rotation.

In the example method, the knob axis of rotation may be coaxial with the main axis, the knob may be configured to rotate with the inner rod and movable axially along the handle, the handle may define a handle cavity extending axially through the distal handle end to a linear translation portion including a plurality of handle threads defined therein, the proximal rod end of the inner rod may extend past a proximal tube end of the driver tube and at least partially into the linear translation portion of the handle cavity and may include a plurality of proximal rod threads configured to threadingly engage one or more of the plurality of handle threads, the method may further comprise simultaneous rotating about and axial translating of the inner rod along the main axis in response to the knob being rotated about the knob axis of rotation.

In the example method, the knob axis of rotation may be coaxial with the main axis, the knob may be configured to rotate with the inner rod, the handle may comprise a free swivel coupled to the handle and extend axially beyond the knob to define the proximal handle end, the method further comprise: rotating the free swivel about the main axis completely independently from rotation of the knob and the handle; and rotating the inner rod about the main axis in response to the knob being rotated about the knob axis of rotation.

BRIEF DESCRIPTION OF THE DRAWINGS

For a detailed description of example embodiments, reference will now be made to the accompanying drawings in which.

DEFINITIONS

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"Throughbore" shall mean an aperture or passageway through an underlying object. However, the term "throughbore" shall not be read to imply any method of creation. Thus, a throughbore may be created in any suitable way, such as drilling, boring, laser drilling, or casting.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various examples are directed to marker deployment systems and corresponding methods of operation for deploying bone markers used in medical procedures. More particularly, various examples are directed to example marker deployment systems and corresponding methods of operation in which the marker deployment system may be used in a one-handed fashion to improve control and efficiency of the placement of the bone marker by a surgeon. In the example marker deployment systems, a handle extends radially from and longitudinally along a main axis from a proximal handle end to a distal handle end. A driver tube is coupled to and extends from the handle at the distal handle end along the main axis from a proximal tube end to a distal tube end. The driver tube defines a tube bore extending axially therethrough and the distal tube end is configured to support a bone marker. An inner rod of the example marker deployment systems extends axially through the driver tube from a proximal rod end to a distal rod end. The distal rod end includes a plurality of distal rod threads comprising a retention fastener configured to engage and selectively secure the bone marker at the distal tube end. A knob is operably coupled to the inner rod and is rotatable about a knob axis of rotation extending along the main axis. The knob is rotatable in a first direction to secure the bone marker and in a second direction opposite the first direction to release the bone marker. At least a portion of the handle extends axially beyond the knob to define the proximal handle end. The specification first turns to an example surgical system employing the example marker deployment systems to orient the reader.

Figure 1:
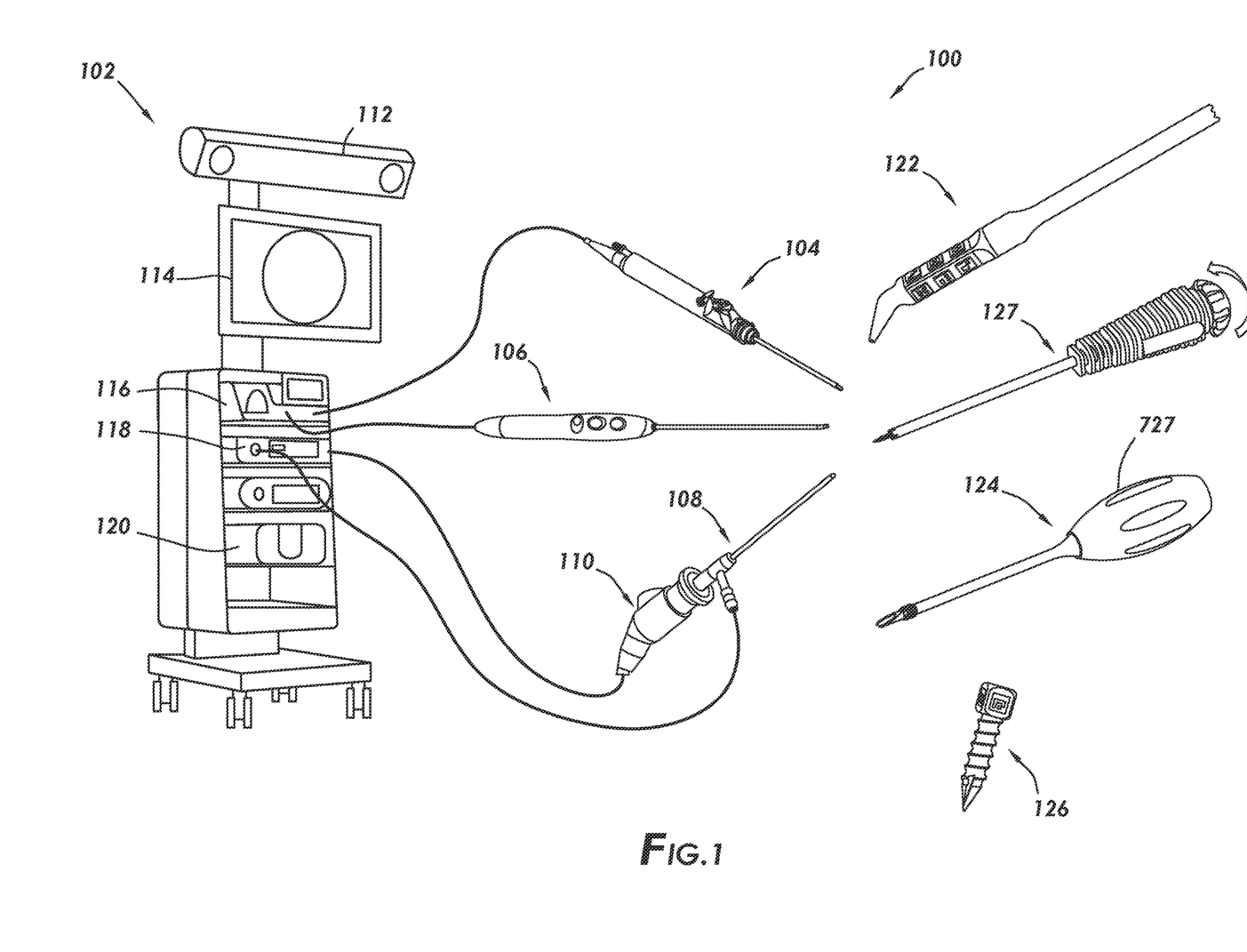
FIG. 1 shows a surgical system in accordance with at least some embodiments.

FIG. 1 shows a surgical system (not to scale) in accordance with at least some embodiments. In particular, the example surgical system 100 comprises a tower or device cart 102, an example mechanical resection instrument 104, an example plasma-based ablation instrument (hereafter just ablation instrument 106), and an endoscope in the example form of an arthroscope 108 and attached camera head 110. The device cart 102 may comprise a camera 112 (illustratively shown as a stereoscopic camera), a display device 114, a resection controller 116, and a camera control unit (CCU) together with an endoscopic light source and video controller. In example cases the CCU, endoscopic light source, and video controller not only provide light to the arthroscope 108 and displays images received from the camera head 110, but also implement various additional aspects, such as tracking location of objects within the surgical site. Thus, the CCU, endoscopic light source, and video controller are hereafter referred to as a surgical controller 118. In other cases, however, the CCU, endoscopic light source, and video controller may be a separate and distinct systems from the controller that handles aspects of intraoperative tracking, yet the separate devices would nevertheless be operationally coupled.

The example device cart 102 further includes a pump controller 120 (e.g., single or dual peristaltic pump). Fluidic connections of the mechanical resection instrument 104 and ablation instrument 106 are not shown so as not to unduly complicate the figure. Similarly, fluidic connections between the pump controller 120 and the patient are not shown so as not to unduly complicate the figure. In the example system, both the mechanical resection instrument 104 and the ablation instrument 106 are coupled to the resection controller 116 being a dual-function controller. In other cases, however, there may be a mechanical resection controller separate and distinct from an ablation controller. The example devices and controllers associated with the device cart 102 are merely examples, and other examples include vacuum pumps, robotic arms holding various instruments, ultrasonic cutting devices and related controllers, patient-positioning controllers, and robotic surgical systems.

FIG. 1 further shows additional instruments that may be present during an arthroscopic surgical procedure. In particular, FIG. 1 shows an example touch probe 122, an aimer 124, a bone marker 126, and a marker deployment system 127, 727 or installation tool for the bone marker 126. The touch probe 122 may be used during the surgical procedure to provide information to the surgical controller 118, such as: information to register a three-dimensional bone model to an underlying bone visible in images captured by the arthroscope 108 and camera head 110; and information as to a revised tunnel-entry location and/or a revised tunnel-exit location when the surgeon elects to deviate from the preoperative tunnel plan. The aimer 124 may be used as a guide for placement and drilling with a drill wire to create an initial or pilot tunnel through the bone. The bone marker 126 may be rigidly attached to the bone by the marker deployment system 127 and serve as an anchor location for the surgical controller 118 to know the orientation of the bone (e.g., after registration of a three-dimensional bone model). Additional tools and instruments will be present, such as the drill wire, various reamers for creating the throughbore and counterbore aspects of a tunnel through the bone, and various tools, such as for suturing and anchoring a graft. These additional tools and instruments are not shown so as not to further complicate the figure.

Figure 2:
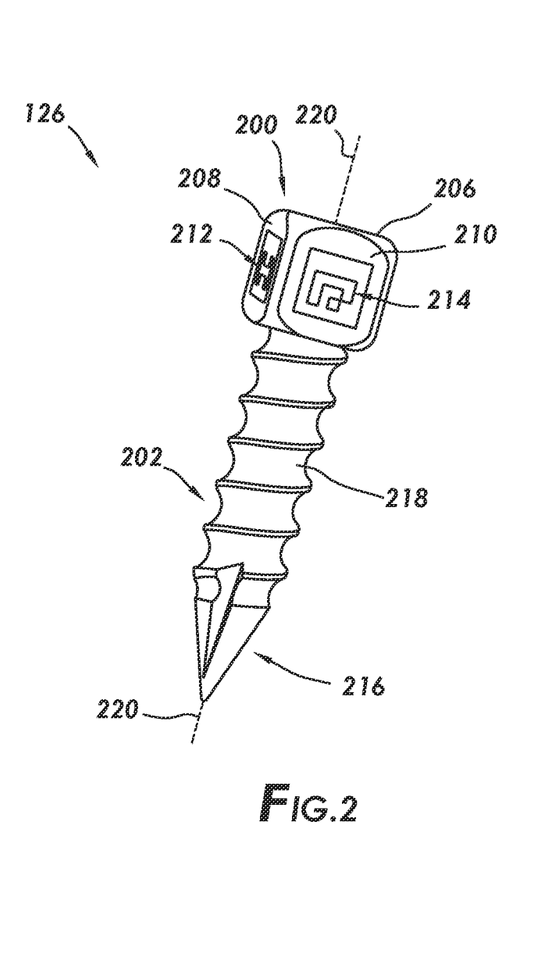
FIG. 2 shows a perspective side view of a bone marker in accordance with at least some embodiments.

FIG. 2 shows a perspective side view of an example bone marker 126. In particular, the example bone marker 126 comprises a polyhedron 200, an externally-threaded screw 202. The example polyhedron 200 defines an upper surface or upper face 206, and a plurality of outward-facing surfaces, such as outward-facing surface 208 and outward-facing surface 210. In the example of FIG. 2, the polyhedron 200 is a cube, and thus two additional outward-facing surfaces are present but are not visible in the view of FIG. 2. However, the polyhedron 200 may take any suitable shape which defines an upper face 206, at least three outward-facing surfaces, and a location (e.g., a lower face) from which the externally-threaded screw 202 protrudes. Each of the outward-facing surfaces, such as outward-facing surfaces 208 and 210 visible in FIG. 2, have disposed thereon a fiducial pattern, such as fiducial patterns 212 and 214, respectively. Referring to fiducial pattern 214 as representative, the fiducial pattern 214 is a machine readable code that uniquely identifies the outward-facing surface 210 of the polyhedron 200. That is, the surgical controller 118 (FIG. 1), receiving images captured by the arthroscope 108 (FIG. 1) and camera head 110 (FIG. 1), may read a value represented by the fiducial pattern 214. Moreover, the fiducial pattern 214 is designed and constructed such that, by analyzing a physical relationships of the three-dimensional features or patterns of the fiducial pattern 214 (e.g., outside corners, inside corners, relative line widths) within the images of the fiducial pattern 214, the surgical controller 118 may thus determine the physical orientation of the fiducial pattern and thus the bone marker 126 in the three-dimensional coordinate space in the view of the arthroscope 108. It follows that, when the bone marker 126 is coupled to a bone, the surgical controller 118 may determine the physical orientation of the attached bone in the three-dimensional coordinate space in the view of the arthroscope 108. In example systems, the fiducial pattern on each of the outward-facing surfaces is a unique and distinct pattern.

In the example, the externally-threaded screw 202 projects from a side of the polyhedron 200 opposite from the upper face 206. In example cases, the polyhedron 200 and the externally-threaded screw 202 are a monolithic structure, such as a continuous piece of metallic material (e.g., aluminum). For example, the polyhedron 200 and the externally-threaded screw 202 may be simultaneously cast within a mold, or may be milled from single piece of aluminum, stainless steel, or titanium. The example externally-threaded screw 202 is a self-drilling or self-tapping screw, meaning that the distal end 216 of the externally-threaded screw 202 comprises a drilling feature to create the initial aperture into the bone. The externally-threaded screw 202 further comprises threads 218 extending from near the distal end 216 toward the proximal end of the externally-threaded screw 202. In some cases the threads 218 are right-handed threads, meaning the bone marker 126 is turned clockwise about its longitudinal central axis 220, viewed from above the polyhedron 200 looking along the longitudinal central axis toward the externally-threaded screw, when the bone marker 126 is being screwed into a bone. The threads 218 may alternatively be left-handed threads.

The bone marker 126 is a relatively small object—in one example the outside diameter of the externally-threaded screw 202 is about 2.5 millimeters (mm)—though larger and smaller sizes are contemplated. In example cases, the polyhedron 200 may form faces that are about 4 mm in length (measured parallel to the longitudinal central axis 220). The overall length of example bone markers may be from 10 mm to 15 mm, inclusive, and in one example 12 mm.

Figure 3:
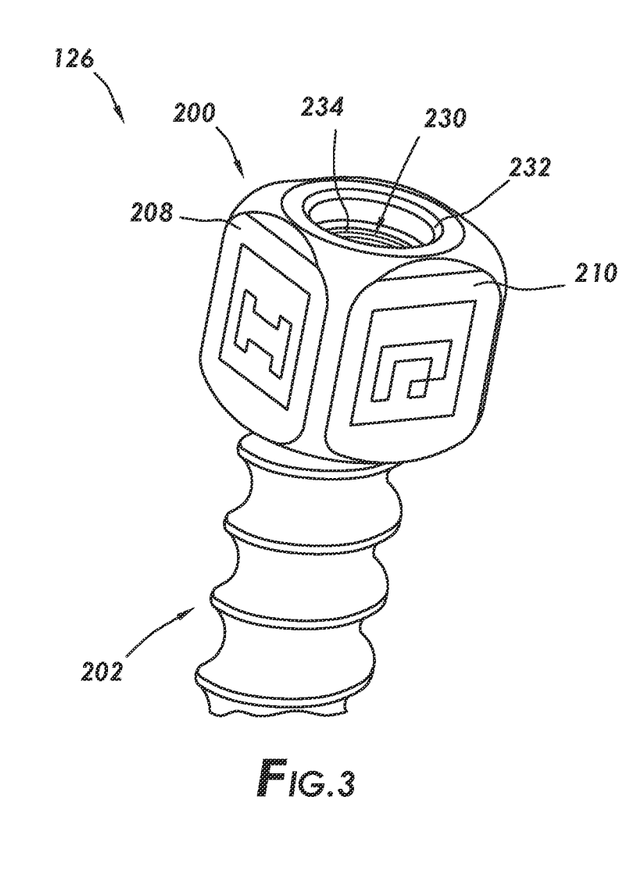
FIG. 3 shows a perspective side view of a bone marker in accordance with at least some embodiments.

FIG. 3 shows a perspective view of the example bone marker 126. In particular, visible in FIG. 3 is the polyhedron 200 and a portion of the externally-threaded screw 202. The outward-facing surfaces 208 and 210 are also visible, with their respective fiducial patterns (not specifically numbered).

Still referring to FIG. 3, the example bone marker 126 further comprises a retention bore 230 having an entrance aperture 232 through the upper face 206 of the polyhedron 200. The retention bore 230 defines a retention feature 234, illustratively shown as threads on an inside surface of the retention bore 230. The retention feature 234 may be used to retain the bone marker 126 in operational relationship with the marker deployment system 127, 727 (not shown in FIG. 3) such that the un-installed bone marker 126 may be placed through the port through the patient's skin, and then screwed in place into the bone. Once screwed in place, the marker deployment system 127, 727 may release from the retention feature 234, enabling the marker deployment system 127, 727 to be withdrawn and leaving the bone marker 126 in place.

Figures 4A, 4B, 5:
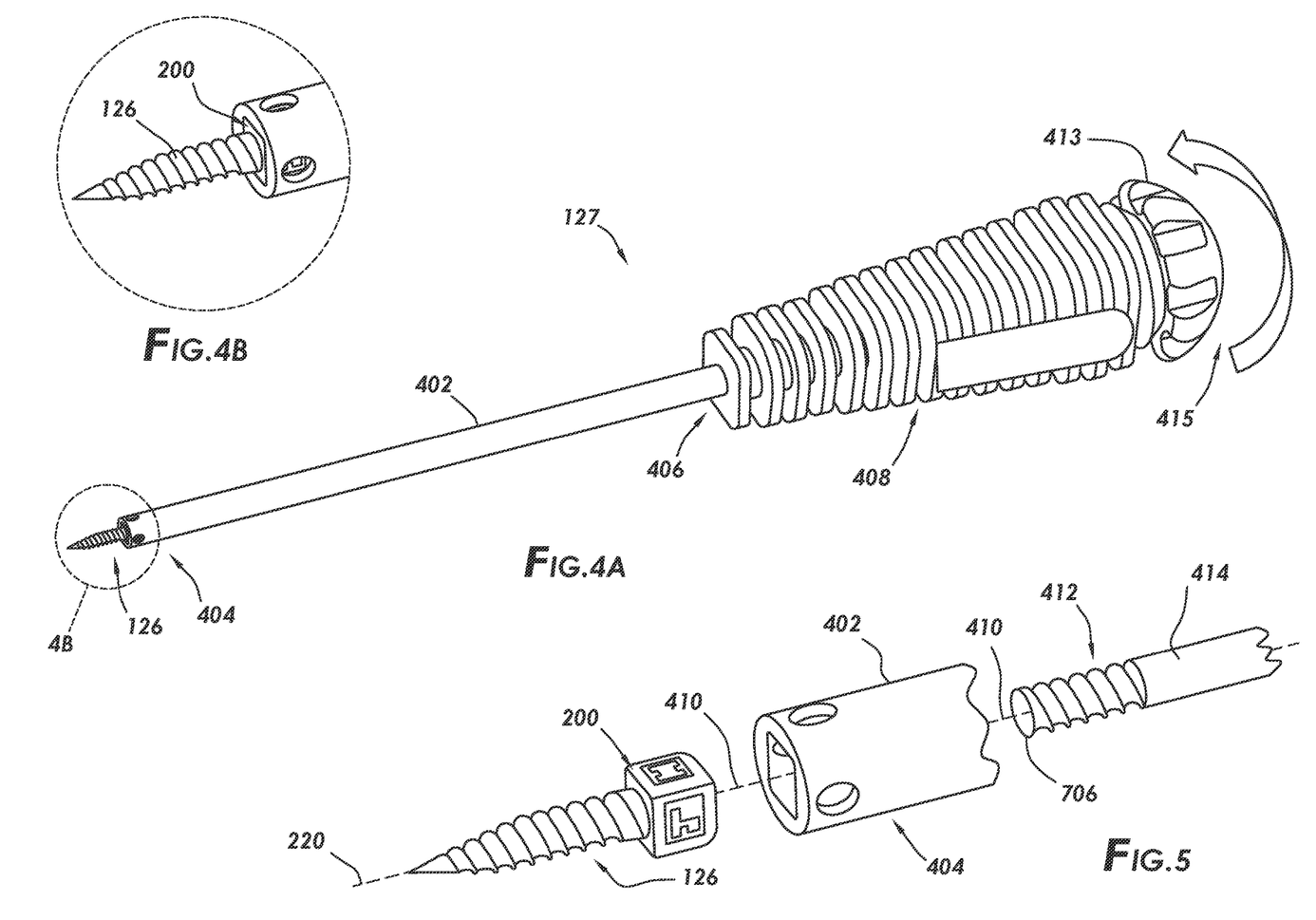
FIGS. 4A and 4B show a perspective view of a bone marker retained on a distal end of a marker deployment system in accordance with at least some embodiments.
FIG. 5 shows an exploded perspective view of the distal end of the marker deployment system and the bone marker, in accordance with at least some embodiments.

FIG. 4A shows a perspective view of the bone marker 126 retained on a distal end of an example marker deployment system 127. In particular, FIG. 4A shows an example marker deployment system 127 comprising an elongate shaft or driver tube 402 defining a distal tube end 404 and a proximal tube end 406. The driver tube 402 is coupled on the proximal tube end 406 to a handle 408. Though not visible in FIG. 4A, the driver tube 402 and handle 408 define coaxial throughbores. Also visible in FIG. 4A is the example bone marker 126. FIG. 4B shows a magnified view of the distal tube end 404 comprising the bone marker 126. In the example, the bone marker 126 is retained within the marker deployment system 127 by the telescoping the polyhedron 200 into an internal volume at the distal tube end 404 of the marker deployment system 127. As will be shown and discussed in greater detail below, the bone marker 126 is retained in the telescoped relationship by way of a retention fastener (not visible in FIG. 4A or 4B) placed in mating relationship with a retention feature 234 (FIG. 2) within the retention bore 230 (FIG. 2). The retention fastener provides an axial force tending to hold the bone marker 126 in the telescoped relationship. Retaining the bone marker 126 within the marker deployment system 127 enables installation of the bone marker 126 directly, and eliminates the related-art approach of drilling a pilot tunnel with a guide wire and then sliding the bone marker along the guide to direct the bone marker to the correct location on the bone.

During use, the distal tube end 404 of the marker deployment system 127 and the retained bone marker 126 are placed within the surgical site, such as through a port through the patient's skin. The marker deployment system 127 may then be used to not only place the bone marker 126 in a suitable location for installation (e.g., in the intercondylar notch for an ACL repair/replacement), but also to provide rotational force to the bone marker 126 to enable the externally-threaded screw 202 to enter the bone and affix the bone marker 126 to the bone. In order to reduce the chances of denting or damaging the fiducial patterns on the outward-facing surfaces of the polyhedron 200, in example cases the rotational force applied to the polyhedron 200 by the marker deployment system 127 is at a location on each of the outward-facing surfaces that does not touch or overlap the respective fiducial pattern on the outward-facing surfaces. Stated otherwise, the rotational force for installation of the bone marker 126 is applied on each outward-facing surface at a location outside the boundaries of the respective fiducial pattern.

FIG. 5 shows an exploded perspective view of the distal end of the marker deployment system 127, 727 and the bone marker 126. In particular, the distal tube end 404 of the driver tube 402 defines an inside surface designed and constructed to telescope over the polyhedron 200 of the bone marker 126. In the example case of the polyhedron 200 being a cube, the inside surface of the distal tube end 404 of the elongate shaft thus defines a square cross-sectional shape. The driver tube 402 further defines a throughbore or tube bore along the main axis 410 of the driver tube 402. The tube bore intersects the inside surface creating a shoulder region (not specifically shown) that limits axial translation of the polyhedron 200 into the distal tube end 404. Telescoped within the tube bore and along the main axis 410 is a retention fastener 412 illustratively shown as an externally threaded portion of an elongate rod or inner rod 414. In the example marker deployment system of FIGS. 4A and 4B, the inner rod 414 may extend to and through handle 408 (FIG. 4A) to the distal tube end 404. The inner rod 414 can be attached to and rotated by a knob 413 at a proximal handle end 415 of the handle 408.

Retaining the bone marker 126 on the distal tube end 404 of the marker deployment system 127, 727 may thus comprise telescoping the polyhedron 200 into the internal volume defined by the inside surface at the distal tube end 404 of the marker deployment system 127, 727. The retention fastener 412 may then be coupled to retention feature 234 (FIG. 2) within the retention bore 230 (FIG. 2) on the upper face of the polyhedron 200. In the example shown, the retention fastener 412 in the form of external threads may threadingly couple to the retention feature 234 in the form of internal threads within the retention bore 230. The inner rod 414 may thus provide a force tending to hold the bone marker 126 in mating relationship with the marker deployment system 127. In the example, when the bone marker 126 is retained in mating relationship with the marker deployment system 127, 727, the longitudinal central axis 220 of the bone marker 126 is coaxial with the main axis 410 of the throughbore of the driver tube 402 and the inner rod 414. In other cases, however, the longitudinal central axis and main axis 410 need not be coaxial.

Once the bone marker 126 is placed in the bone, the retention fastener 412 may be detached from the retention bore 230 (FIG. 2). In particular, in the example case of the retention fastener 412 being external threads, the marker deployment system 127, 727 may be used to hold the bone marker 126 in a constant rotational orientation while the external threads of the retention fastener 412 are unscrewed from mating relationship. In some cases, the threads of the example retention fastener 412 are right-handed threads, but the given that the bone marker 126 may be held in place with the marker deployment system 127, 727, unscrewing the threads of the example retention fastener 412 does not unscrew the bone marker 126 from the bone. In other cases, however, the threads of the example retention fastener 412 may be left-handed threads and the threads of the externally-threaded screw 202 may be right-handed threads (or vice versa), such that the act of unscrewing the threads of the example retention fastener 412 will tend to further tighten the connection of the bone marker 126 to the underlying bone.

Figure 6:
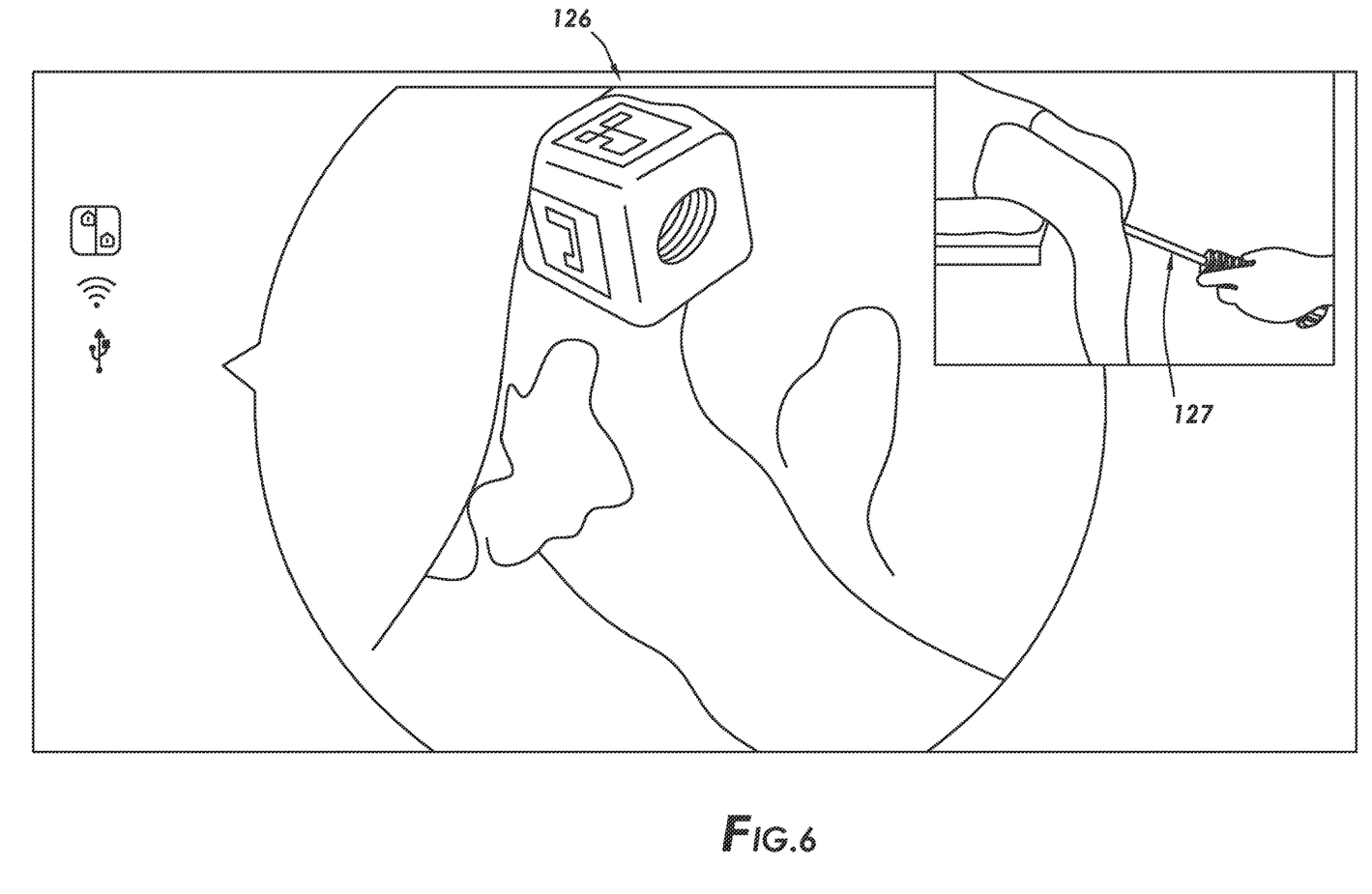
FIG. 6 shows placement of the bone marker in a bone by a surgeon using the marker deployment system of FIGS. 4A and 4B.

FIG. 6 shows placement of the bone marker 126 in a bone by a surgeon (inset) using the marker deployment system 127 of FIGS. 4A and 4B. While the example marker deployment system 127 shown in FIGS. 4A and 4B is well suited to placing the bone marker 126, use of the marker deployment system 127 to screw or unscrew the threads of the example retention fastener 412 typically requires that two hands are used (one to hold the handle 408 and another to turn knob 413). Such two handed operation is a result of the knob 413 being located at the proximal handle end 415 of the handle 408. Accordingly, the surgeon must use both hands to use the marker deployment system 127, while an assistant operates the endoscope (e.g., arthroscope 108), for example. Two handed operation can slow down the speed and efficiency of the overall surgical procedure.

Consequently, referring now to FIGS. 7-12, example marker deployment systems 727 that may be operated in a one-handed fashion are shown. The example marker deployment systems 727 include a handle 408 extending radially from and longitudinally along a main axis 410 from a proximal handle end (not shown) to a distal handle end 700. As in the above example marker deployment system 127, the marker deployment system 727 of FIGS. 7-12 also includes a driver tube 402 coupled to and extending from the handle 408 at the distal handle end 700 along the main axis 410 from a proximal tube end 406 to a distal tube end 404 and defining a tube bore 702 extending axially therethrough. The distal tube end 404 is configured to support the bone marker 126. In addition, the marker deployment system 727 includes an inner rod 414 extending axially through the driver tube 402 from a proximal rod end 704 to a distal rod end 706 (FIG. 5) including a plurality of distal rod threads comprising a retention fastener 412 configured to engage and selectively secure the bone marker 126 at the distal tube end 404. So, for the example marker deployment systems 727 of FIGS. 7-12, the distal tube end 404 and inner rod 414 extending axially through the driver tube 402 to the distal rod end 706 and operation of the retention fastener 412 are the same as for the example marker deployment system 127 shown in FIG. 5. Similar to the example marker deployment system 127 of FIGS. 4A and 4B, the marker deployment systems 727 also includes a knob 713 operably coupled to the inner rod 414 and rotatable about a knob axis of rotation 708 extending along the main axis 410 in a first direction to secure the bone marker 126 and in a second direction opposite the first direction to release the bone marker 126. However, in contrast to the example marker deployment system 127 of FIGS. 4A and 4B, at least a portion of the handle 408 extends axially beyond the knob 713 to define the proximal handle end 415.

Figure 7:
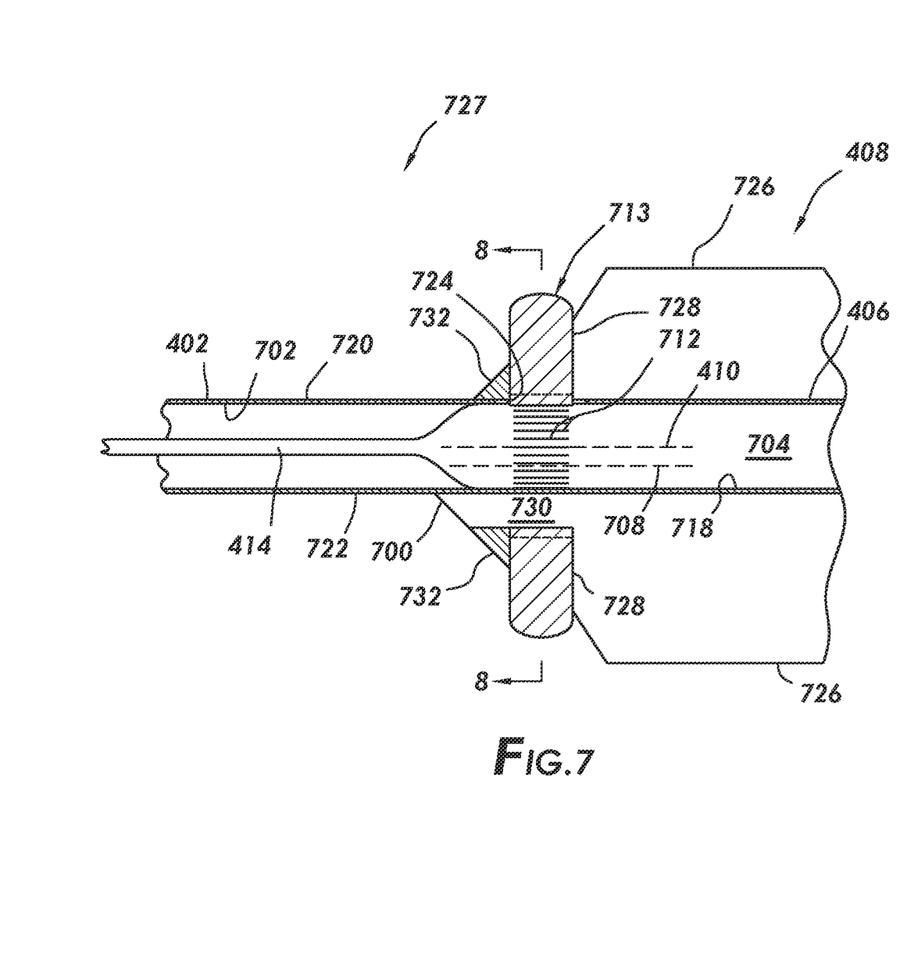
FIG. 7 is a cross-sectional view of an example marker deployment system taken along a main axis that may be operated in a one-handed fashion, in accordance with at least some embodiments.
Figure 8:
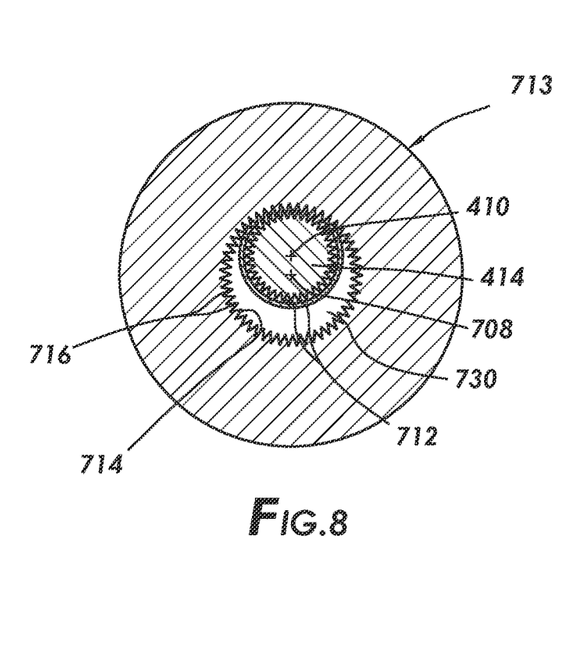
FIG. 8 is a cross-sectional view of the example marker deployment system of FIG. 7 along line 8-8 of FIG. 7 in accordance with at least some embodiments.

Referring specifically to the example marker deployment system 727 of FIGS. 7-8, the knob axis of rotation 708 is offset and parallel to the main axis 410. The inner rod 414 includes a plurality of rod teeth 712 extending radially outwardly therefrom and adjacent the proximal rod end 704. The knob 713 is annularly shaped to define a knob opening 714. The knob 713 includes a plurality of knob teeth 716 extending radially inwardly into the knob opening 714. The plurality of knob teeth 716 are configured to meshingly engage one or more of the plurality of rod teeth 712 to rotate the inner rod 414 about the main axis 410 as the knob 713 is rotated about the knob axis of rotation 708.

In more detail, the handle 408 defines a handle through-bore or handle cavity 718 extending along the main axis 410 and the driver tube 402 extends axially into the handle cavity 718. The driver tube 402 includes a top tube portion 720 and a bottom tube portion 722 and defines a gear window 724 extending through the driver tube 402 into the tube bore 702. The gear window 724 is disposed on the top tube portion 720 and is configured to enable the plurality of knob teeth 716 to meshingly engage the one or more of the plurality of rod teeth 712. The handle 408 extends radially outwardly to a peripheral surface 726 configured to be held in one hand of a user. The handle 408 includes a knob support wall 728 extending radially outwardly from the handle cavity 718 to the peripheral surface 726 proximate the distal handle end 700 of the handle 408. The handle 408 also includes a tube support portion 730 extending axially away from the knob support wall 728 and along the bottom tube portion 722 of the driver tube 402. The tube support portion 730 also extends axially through the knob opening 714 to define the distal handle end 700 of the handle 408. The tube support portion 730 is configured to abut at least some of the plurality of knob teeth 716. At least one of the knob 713 and the handle 408 are configured to retain the knob 713 axially and enable the user to turn the knob 713. According to an aspect, the handle 408 additionally includes a knob retaining ring 732 annularly extending about and engaging the driver tube 402 and the tube support portion 730 of the handle 408. The knob retaining ring 732 is configured to retain the knob 713 axially in sliding abutment with the knob support wall 728 and enable the user to turn the knob 713 with the one hand and enable rotation of the knob 713 about the knob axis of rotation 708. While the knob retaining ring 732 is shown, it should be appreciated that other structures or arrangements may be employed instead to prevent the knob 713 from translating distally. For example, the knob 713 may be a split knob configured to be retained on the handle 408.

So, the example marker deployment system 727 shown in FIGS. 7-8 employs the inner rod 414, which is configured as a pinion gear (i.e., the plurality of rod teeth 712) and mated to the knob 713 with a mating internal gear (i.e., the plurality of knob teeth 716). In addition, the knob 713 is eccentric relative to the main axis 410. This arrangement includes a window or the gear window 724 in the driver tube 402 which enables the knob 713 to be located at the most distal end (i.e., distal handle end 700 of the handle 408), under the user's thumb/forefinger. Once the fiducial or bone marker 126 is placed in the bone (e.g., condylar bone), the user can rotate the knob 713 without repositioning their hand on the handle 408 and without assistance. The rotation of the knob 713 is transferred to the distal rod end 706 of the inner rod 414, releasing, or capturing the bone marker 126 from the driver tube 402.

Figure 9:
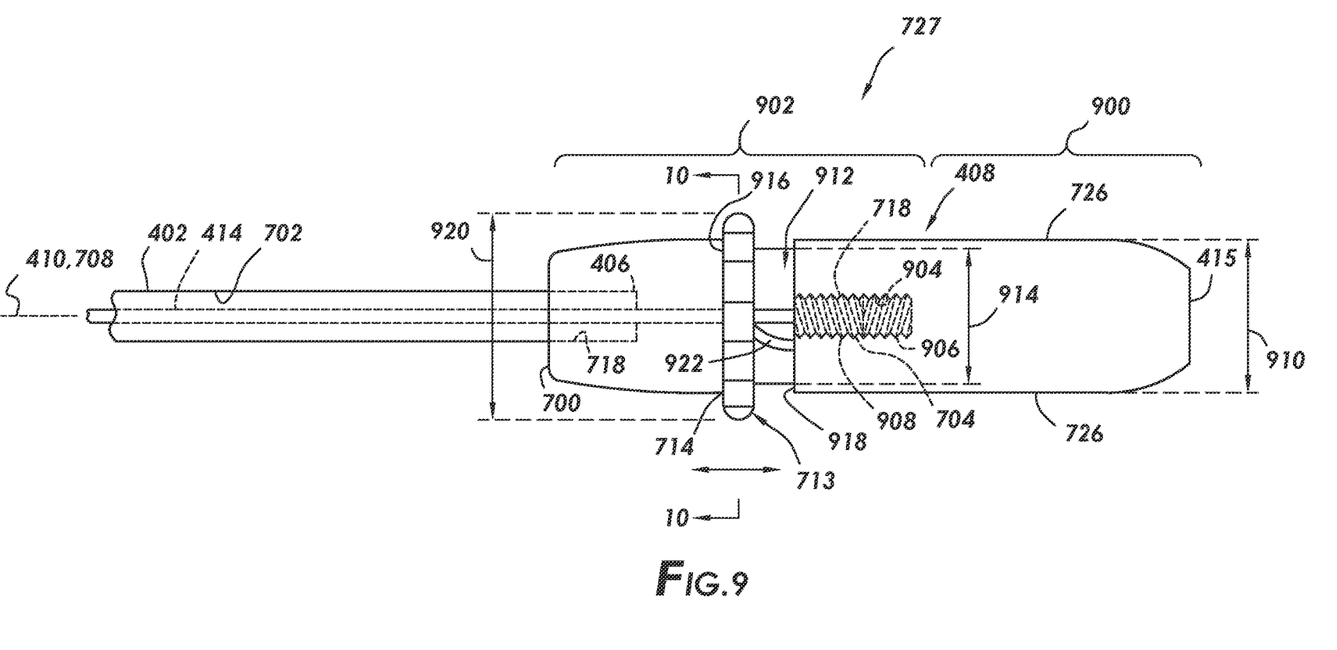
FIG. 9 is a side view of another example marker deployment system taken along the main axis that may be operated in a one-handed fashion, in accordance with at least some embodiments.
Figure 10:
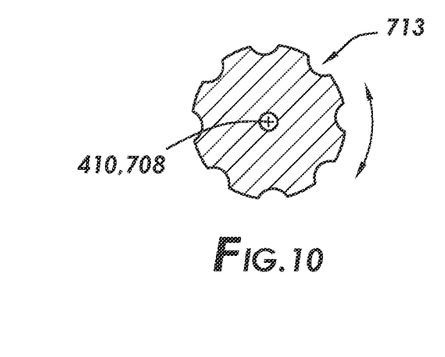
FIG. 10 is a cross-sectional view of the example marker deployment system of FIG. 9 along line 10-10 of FIG. 9 in accordance with at least some embodiments.

Now referring specifically to FIGS. 9-10, another example marker deployment system 727 is shown. The marker deployment system 727 includes the handle 408 extending radially from and longitudinally along the main axis 410 from the proximal handle end 415 to the distal handle end 700 to define a proximal half 900 of the handle 408 adjacent the proximal handle end 415 and a distal half 902 of the handle 408 adjacent the distal handle end 700. As in the example marker deployment system 727 of FIGS. 7-9, the driver tube 402 is coupled to and extends from the handle 408 at the distal handle end 700 along the main axis 410 from the proximal tube end 406 to a distal tube end (FIG. 5). The driver tube 402 defines the tube bore 702 extending axially therethrough. The distal tube end 404 is configured to support the bone marker 126. Again, the inner rod 414 extends axially through the driver tube 402 from the proximal rod end 704 to the distal rod end 706 (FIG. 5) that includes a plurality of distal rod threads comprising the retention fastener 412 configured to engage and selectively secure the bone marker 126 at the distal tube end 404. The knob 713 is operably coupled to the inner rod 414 and rotatable about the knob axis of rotation 708 extending along the main axis 410. The inner rod 414 is rotatable in a first direction to secure the bone marker 126 and in a second direction opposite the first direction to release the bone marker 126. As shown, the knob 713 is disposed in the distal half 902 of the handle 408.

Still referring to FIGS. 9-10, the knob axis of rotation 708 is coaxial with the main axis 410. The knob 713 rotates with the inner rod 414 and is movable axially along the handle 408. The handle 408 defines handle cavity 718 extending axially through the distal handle end 700 to a linear translation portion 904 including a plurality of handle threads 906 defined therein. The proximal rod end 704 extends past the proximal tube end 406 of the driver tube 402 and at least partially into the linear translation portion 904 of the handle cavity 718. The proximal rod end 704 includes a plurality of proximal rod threads 908 configured to threadingly engage one or more of the plurality of handle threads 906 and cause simultaneous rotation about and axial translation of the inner rod 414 along the main axis 410 as the knob 713 is rotated about the knob axis of rotation 708.

More specifically, the driver tube 402 partially extends axially into the handle cavity 718. The handle 408 extends radially outwardly a first diameter 910 to the peripheral surface 726 that is configured to be held in one hand of a user. The handle 408 includes a knob sliding portion 912 having a second diameter 914 less than the first diameter 910 to define a distal knob shoulder 916 between the peripheral surface 726 and the knob sliding portion 912 and a proximal knob shoulder 918 between the peripheral surface 726 and the knob sliding portion 912, the distal knob shoulder 916 configured to abut the knob 713 in a marker locked position of the knob 713 (i.e., as far axially as the knob 713 can move toward the distal handle end 700) and the proximal knob shoulder 918 configured to abut the knob 713 in a marker unlocked position of the knob 713 (i.e., as far axially as the knob 713 can move toward the proximal handle end 415). The knob 713 extends radially outwardly a third diameter 920 greater than the first diameter 910. The knob 713 is annularly shaped to define a knob opening 714 configured to surround and slidingly abut the knob sliding portion 912 and includes at least one knob pin (not shown) extending radially inwardly. The knob sliding portion 912 defines at least one rod engagement slot 922 and the at least one knob pin extends through the at least one rod engagement slot 922 and attaches the knob 713 to the inner rod 414 to fix the inner rod 414 for rotation with the knob 713. The at least one rod engagement slot 922 and knob sliding portion 912 are configured to enable the user to turn the knob 713 with the one hand and provide limited axial movement of the knob 713 as the knob 713 is simultaneously rotated about the knob axis of rotation 708 and axially translated along the main axis 410. According to an aspect, the plurality of proximal rod threads 908 may be different than the plurality of handle threads 906 of the linear translation portion 904 of the handle cavity 718. So, the threads on each end of the inner rod 414 may be different to alter the number of turns for the proximal and distal ends. Specifically, threads of different pitches may separate the number of turns of the knob 713 from the number of engaging turns of the retention fastener 412.

Thus, in the example marker deployment system 727 of FIGS. 9-10, once the fiducial or bone marker 126 is placed in the bone, the user can rotate the knob 713 using their thumb/forefinger. The rotation of the knob 713 is transferred to both the proximal and distal ends of the inner rod 414. On the proximal rod end, the inner rod 414 is engaged with threads in the handle 408 (i.e., the plurality of handle threads 906 in the linear translation portion 904), creating linear translation. The rotation on the distal rod end 706 of the inner rod 414 releases or captures the bone marker 126 from the driver tube 402.

Figure 11:
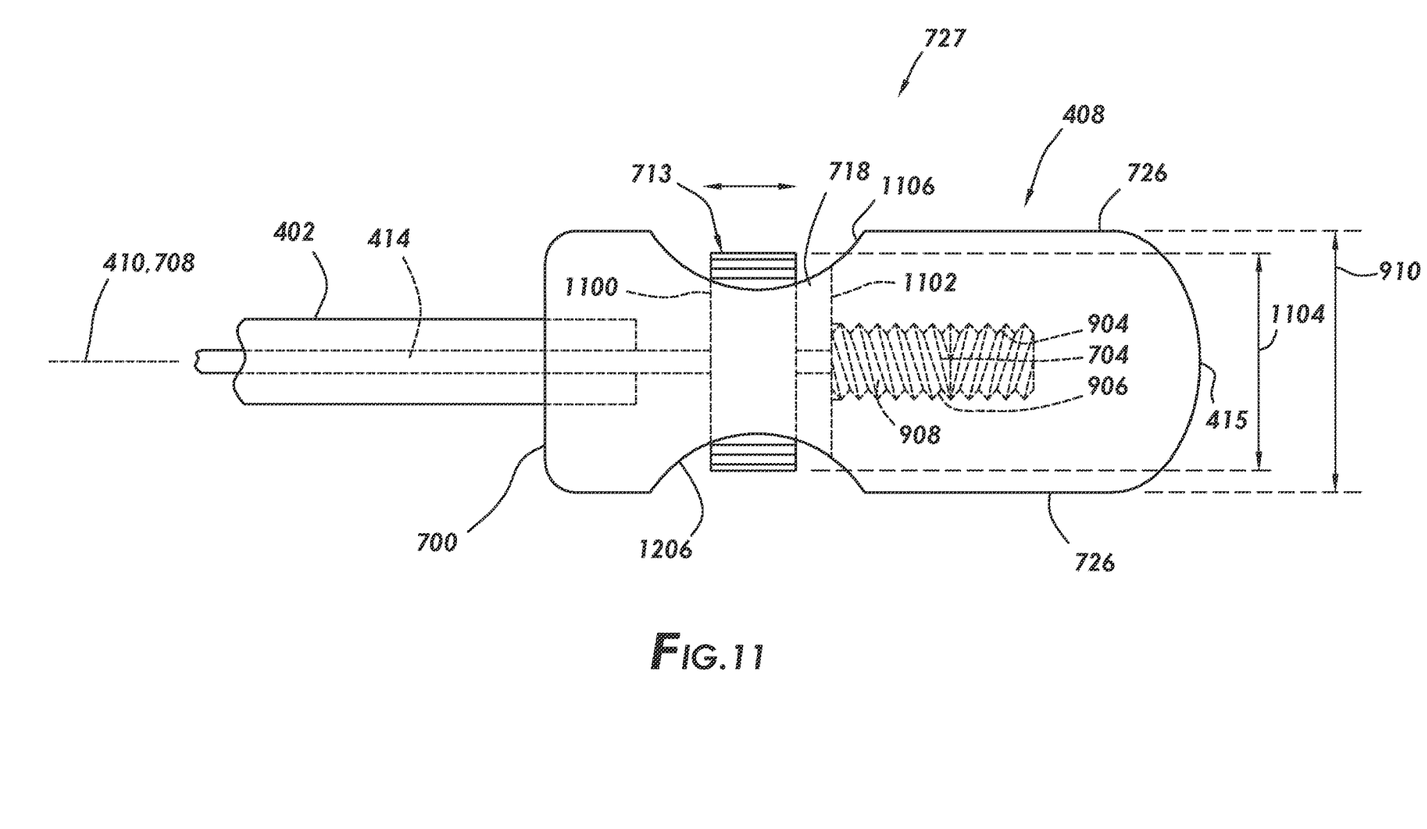
FIG. 11 is a side view of yet another example marker deployment system taken along the main axis that may be operated in a one-handed fashion, in accordance with at least some embodiments.

Now referring specifically to FIG. 11, yet another example marker deployment system 727 is shown. Similar to the example shown in FIGS. 9-10, the driver tube 402 partially extends axially into the handle cavity 718. Again, the handle 408 extends radially outwardly a first diameter 910 to a peripheral surface 726 configured to be held in one hand of a user. However, the handle 408 includes a distal knob barrier 1100 within the handle cavity 718 and extending radially inwardly from the peripheral surface 726. Similarly, the handle 408 includes a proximal knob barrier 1102 within the handle cavity 718 and extending radially inwardly from the peripheral surface 726. The distal knob barrier 1100 is configured to abut the knob 713 in a marker locked position of the knob 713 (i.e., as far axially as the knob 713 can move toward the distal handle end 700) and the proximal knob barrier 1102 is configured to abut the knob 713 in a marker unlocked position of the knob 713 (i.e., as far axially as the knob 713 can move toward the proximal handle end 415). And in contrast to the example shown in FIGS. 9-10, the knob 713 extends radially outwardly from the inner rod 414 a third diameter 1104 less than the first diameter 910 and is configured to rotate in the handle cavity 718. The handle 408 defines at least one knob access window 1106 extending radially inwardly from the peripheral surface 726 into the handle cavity 718. The at least one knob access window 1106 is configured to enable the user to turn the knob 713 with the one hand and provide limited axial movement of the knob 713 as the knob 713 is simultaneously rotated about the knob axis of rotation 708 and axially translated along the main axis 410.

The one handed operation of the marker deployment system 727 described herein enables the surgeon to hold the endoscope (e.g., arthroscope 108) in one hand and the marker deployment system 727 in the other, providing more overall control and efficiency in the placement of the bone marker 126.

Figure 12:
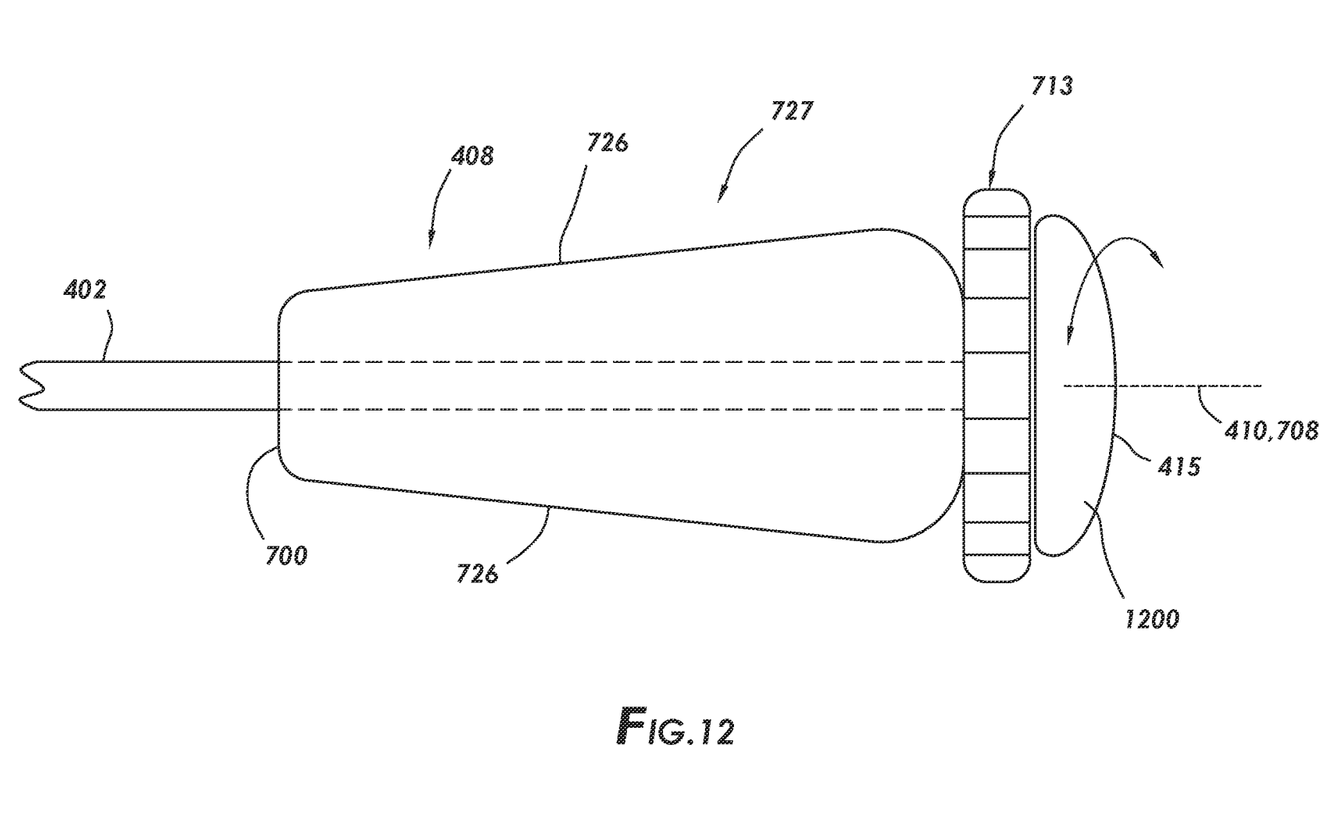
FIG. 12 is a cross-sectional view of a further example marker deployment system taken along the main axis, in accordance with at least some embodiments.

Now referring specifically to FIG. 12, a further example marker deployment system 727 is shown. The knob axis of rotation 708 is coaxial with the main axis 410 and the knob 713 rotates with the inner rod 414. The handle 408 includes a free swivel 1200 coupled to the handle 408. The free swivel 1200 extends axially beyond the knob 713 to define the proximal handle end 415. The free swivel 1200 is rotatable about the main axis 410 completely independently from rotation of the knob 713 and the handle 408. Rotation of the knob 713 causes rotation of the inner rod 414 about the main axis 410 as the knob 713 is rotated about the knob axis of rotation 708.

Figure 13:
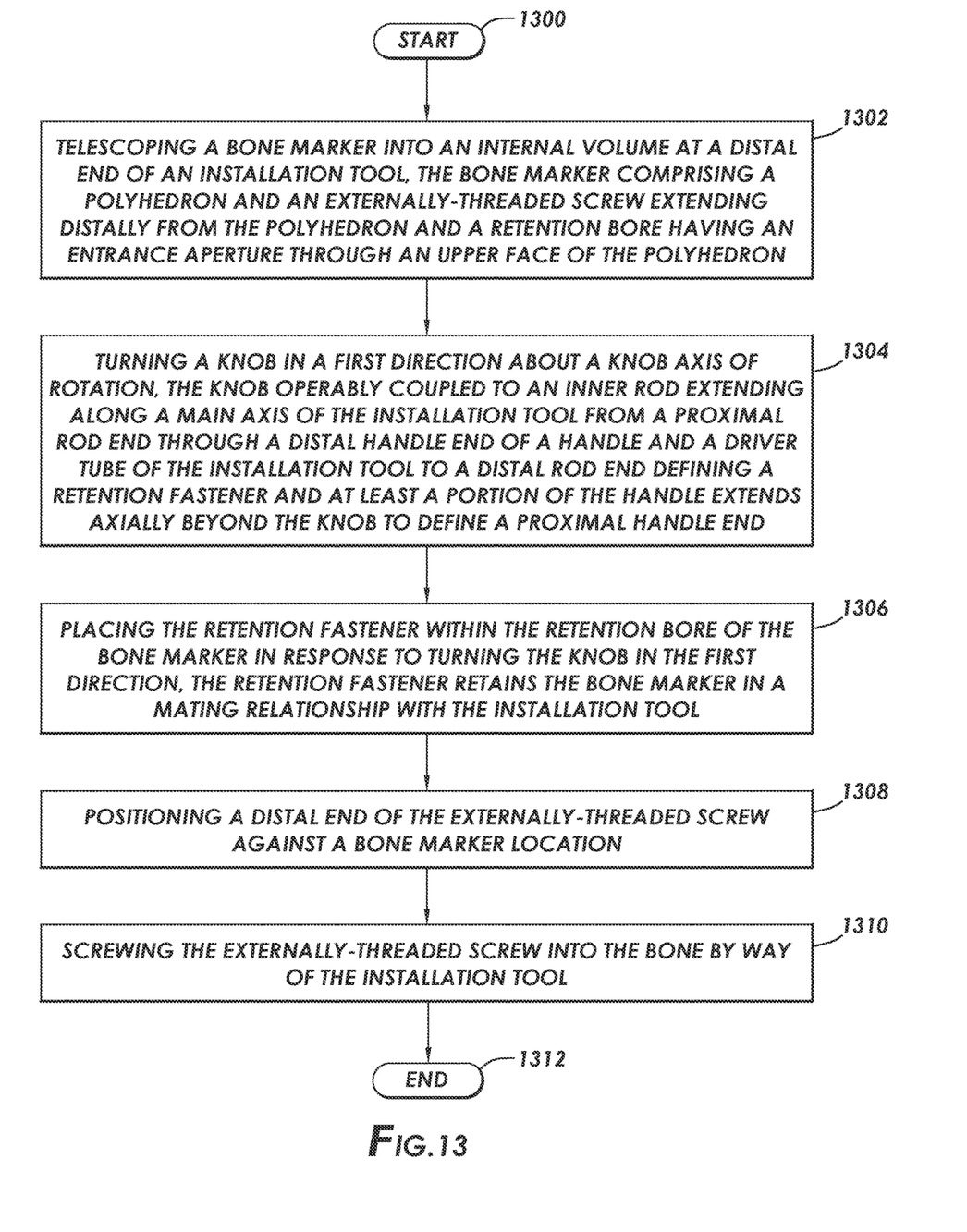
FIG. 13 shows a method of operating the marker deployment system, in accordance with at least some embodiments.

FIG. 13 shows a method of operating the marker deployment system 727 in accordance with at least some embodiments. In particular, the method starts (block 1300) and comprises: telescoping a bone marker 126 into an internal volume at a distal end of an marker deployment system 727, the bone marker 126 comprising a polyhedron 200 and an externally-threaded screw 202 extending distally from the polyhedron 200 and a retention bore 230 having an entrance aperture through an upper face of the polyhedron 200 (block 1302); turning a knob 713 in a first direction about a knob axis of rotation 708, the knob 713 operably coupled to an inner rod 414 extending along a main axis 410 of the marker deployment system 727 from a proximal rod end 704 through a distal handle end 700 of a handle 408 and a driver tube 402 of the marker deployment system 727 to a distal rod end 706 defining a retention fastener 412 and at least a portion of the handle 408 extends axially beyond the knob 713 to define a proximal handle end 415 (block 1304); placing the retention fastener 412 within the retention bore 230 of the bone marker 126 in response to turning the knob 713 in the first direction, the retention fastener 412 retains the bone marker 126 in a mating relationship with the marker deployment system 727 (block 1306); positioning a distal end of the externally-threaded screw 202 against a bone at a marker location (block 1308); and screwing the externally-threaded screw 202 into the bone by way of the marker deployment system 727 (block 1310). Thereafter, the example methods ends (block 1312). According to an aspect, the placing the retention fastener 412 within the retention bore 230 of the bone marker 126 in response to turning the knob 713 in the first direction can further comprise threading distal rod threads of the retention fastener 412 into mating relationship with internal threads of the retention bore 230.

In more detail, the step of turning a knob 713 in a first direction about a knob axis of rotation 708 extending along a main axis 410 of the marker deployment system 727 can further be defined as grasping a peripheral surface 726 of a handle 408 of the marker deployment system 727 with one hand of a user and turning the knob 713 in the first direction about the knob axis of rotation 708 extending along the main axis 410 of the marker deployment system 727 using the one hand of the user.

The method can also include further include, after screwing the externally-threaded screw 202 into the bone, turning the knob 713 in a second direction about the knob axis of rotation 708 opposite the first direction. Next, removing the retention fastener 412 from within the retention bore 230 in response to turning the knob 713 in the second direction. Specifically, the step of turning the knob 713 in a second direction about the knob axis of rotation 708 opposite the first direction can further be defined as grasping a peripheral surface 726 of a handle 408 of the marker deployment system 727 with one hand of a user and turning the knob 713 in the second direction about the knob axis of rotation 708 opposite the first direction using the one hand of the user.

After the bone marker 126 has been screwed into the bone at the marker location by way of the marker deployment system 727 (block 1310), the steps shown in blocks 1302-1306 can be repeated to capture and retrieve the bone marker 126. Specifically, once the bone marker 126 is in the internal volume at the distal end of the marker deployment system 727 and the retention fastener 412 is in the retention bore 230 (block 1306), the user can unscrew the externally-threaded screw 202 from the bone by rotating the handle 408 about the main axis 410 in an opposite direction than used for screwing the externally-threaded screw 202 into the bone (e.g., in the step shown in block 1310). With the bone marker 126 retained in the marker deployment system 727, the bone marker 126 can then be removed from the surgical site.

As discussed above with reference to FIGS. 7-8, the knob axis of rotation 708 is offset and parallel to the main axis 410. The inner rod 414 includes a plurality of rod teeth 712 extending radially outwardly therefrom adjacent the proximal rod end 704. The knob 713 is annularly shaped to define a knob opening 714 and includes a plurality of knob teeth 716 extending radially inwardly into the knob opening 714. The knob teeth 716 are configured to meshingly engage one or more of the plurality of rod teeth 712. Thus, the method can further include the step of rotating the inner rod 414 about the main axis 410 in response to the knob 713 being rotated about the knob axis of rotation 708.

As discussed above with reference to FIGS. 9-11, the knob axis of rotation 708 is coaxial with the main axis 410. The knob 713 rotates with the inner rod 414 and is movable axially along the handle 408. The handle 408 defines handle cavity 718 extending axially through the distal handle end 700 to a linear translation portion 904 including a plurality of handle threads 906 defined therein. The proximal rod end 704 of the inner rod 414 extends past a proximal tube end 406 of the driver tube 402 and at least partially into the linear translation portion 904 of the handle cavity 718 and includes a plurality of proximal rod threads 908. The plurality of proximal rod threads 908 are configured to threadingly engage one or more of the plurality of handle threads 906. So, the method can further include the step of simultaneous rotating about and axial translating of the inner rod 414 along the main axis 410 in response to the knob 713 being rotated about the knob axis of rotation 708. According to an aspect, the proximal rod threads 908 are different than the plurality of handle threads 906 of the linear translation portion 904 of the handle cavity 718.

As discussed above with reference to FIG. 12, the knob axis of rotation 708 is coaxial with the main axis 410, the knob 713 rotates with the inner rod 414. The handle 408 includes a free swivel 1200 coupled to the handle 408 and extending axially beyond the knob 713 to define the proximal handle end 415. Therefore, the method can further include the step of rotating the free swivel 1200 about the main axis 410 completely independently from rotation of the knob 713 and the handle 408. The method can also include the step of rotating the inner rod 414 about the main axis 410 in response to the knob 713 being rotated about the knob axis of rotation 708.

The above discussion is meant to be illustrative of the principles and various embodiments of the present invention. Numerous variations and modifications will become apparent to those skilled in the art once the above disclosure is fully appreciated. It is intended that the following claims be interpreted to embrace such variations and modifications.

What is claimed is:

1. A marker deployment system, comprising:
 a handle extending radially from and longitudinally along a main axis from a proximal handle end to a distal handle end;
 a driver tube coupled to and extending from the handle at the distal handle end along the main axis from a proximal tube end to a distal tube end and defining a tube bore extending axially therethrough, the distal tube end configured to support a bone marker;

an inner rod extending axially through the driver tube from a proximal rod end to a distal rod end including a plurality of distal rod threads comprising a retention fastener configured to engage and selectively secure the bone marker at the distal tube end;

a knob operably coupled to the inner rod and rotatable about a knob axis of rotation extending along the main axis in a first direction to secure the bone marker and in a second direction opposite the first direction to release the bone marker, wherein at least a portion of the handle extends axially beyond the knob to define the proximal handle end; and wherein the knob axis of rotation is coaxial with the main axis, the knob is configured to rotate with the inner rod and movable axially along the handle, the handle defines a handle cavity extending axially through the distal handle end to a linear translation portion including a plurality of handle threads defined therein, and the proximal rod end extends past the proximal tube end of the driver tube and at least partially into the linear translation portion of the handle cavity and includes a plurality of proximal rod threads configured to threadingly engage one or more of the plurality of handle threads and cause simultaneous rotation about and axial translation of the inner rod along the main axis as the knob is rotated about the knob axis of rotation.

2. The marker deployment system as set forth in claim 1, wherein:

the driver tube partially extends axially into the handle cavity;

the handle extends radially outwardly a first diameter to a peripheral surface configured to be held in one hand of a user;

the handle includes a knob sliding portion having a second diameter less than the first diameter to define a distal knob shoulder between the peripheral surface and the knob sliding portion and a proximal knob shoulder between the peripheral surface and the knob sliding portion, the distal knob shoulder configured to abut the knob in a marker locked position of the knob and the proximal knob shoulder configured to abut the knob in a marker unlocked position of the knob;

the knob extends radially outwardly a third diameter greater than the first diameter and is annularly shaped to define a knob opening configured to surround and slidingly abut the knob sliding portion and includes at least one knob pin extending radially inwardly; and the knob sliding portion defining at least one rod engagement slot and the at least one knob pin extends through the at least one rod engagement slot and attaches to the knob to the inner rod to fix the inner rod for rotation with the knob and configured to enable the user to turn the knob with the one hand and provide limited axial movement of the knob as the knob is simultaneously rotated about the knob axis of rotation and axially translated along the main axis.

3. The marker deployment system as set forth in claim 1, wherein the plurality of proximal rod threads are different than the plurality of handle threads of the linear translation portion of the handle cavity.

4. A marker deployment system, comprising:

a handle extending radially from and longitudinally along a main axis from a proximal handle end to a distal handle end to define a proximal half of the handle adjacent the proximal handle end and a distal half of the handle adjacent the distal handle end;

a driver tube coupled to and extending from the handle at the distal handle end along the main axis from a proximal tube end to a distal tube end and defining a tube bore extending axially therethrough, the distal tube end configured to support a bone marker;

an inner rod extending axially through the driver tube from a proximal rod end to a distal rod end including a plurality of distal rod threads comprising a retention fastener configured to engage and selectively secure the bone marker at the distal tube end;

a knob operably coupled to the inner rod and rotatable about a knob axis of rotation extending along the main axis in a first direction to secure the bone marker and in a second direction opposite the first direction to release the bone marker, the knob disposed in the distal half of the handle; and wherein the knob axis of rotation is coaxial with the main axis, the knob is configured to rotate with the inner rod and movable axially along the handle, the handle defines handle cavity extending axially through the distal handle end to a linear translation portion including a plurality of handle threads defined therein, the proximal rod end extends past the proximal tube end of the driver tube and at least partially into the linear translation portion of the handle cavity and includes a plurality of proximal rod threads configured to threadingly engage one or more of the plurality of handle threads and cause simultaneous rotation about and axial translation of the inner rod along the main axis as the knob is rotated about the knob axis of rotation.

5. The marker deployment system as set forth in claim 4, wherein:

the driver tube partially extends axially into the handle cavity;

the handle extends radially outwardly a first diameter to a peripheral surface configured to be held in one hand of a user;

the knob extends radially outwardly from the proximal rod end a third diameter less than the first diameter and is configured to rotate in the handle cavity; and the handle includes at least one knob access window extending radially inwardly from the peripheral surface into the handle cavity and configured to enable the user to turn the knob with the one hand and provide limited axial movement of the knob as the knob is simultaneous rotated and axially translated along the main axis as the knob is rotated about the knob axis of rotation.

* * * * *